United States Patent [19]
Kasting et al.

[11] Patent Number: 5,041,439
[45] Date of Patent: Aug. 20, 1991

[54] PENETRATING TOPICAL PHARMACEUTICAL COMPOSITIONS

[75] Inventors: Gerald B. Kasting, Wyoming; Ellen R. Massaro, Cincinnati; Ronald L. Smith, West Chester; William E. Snyder, Cincinnati, all of Ohio

[73] Assignee: The Procter & Gamble Company, Cincinnati, Ohio

[21] Appl. No.: 616,043

[22] Filed: Nov. 20, 1990

Related U.S. Application Data

[63] Continuation of Ser. No. 874,248, Jun. 13, 1986.

[51] Int. Cl.$^5$ .......................... A61K 7/06; A61K 9/12; A61K 31/54; A61K 31/535
[52] U.S. Cl. ................... 514/227.2; 424/47; 424/70; 514/275; 514/852; 514/880; 514/881; 514/937; 514/944; 514/946; 514/947; 514/969; 514/235.8
[58] Field of Search ..................... 514/275, 237, 227.2

[56] References Cited

U.S. PATENT DOCUMENTS

| | | |
|---|---|---|
| 3,382,247 | 5/1968 | Anthony et al. ................. 260/256.4 |
| 3,535,422 | 10/1970 | Cox et al. ............................. 424/164 |
| 4,070,462 | 1/1978 | Ecker .................................. 424/243 |
| 4,139,619 | 2/1979 | Chidsey ................................ 424/45 |
| 4,299,826 | 11/1981 | Luedders ............................ 424/181 |
| 4,537,776 | 8/1985 | Cooper ................................. 514/424 |
| 4,557,934 | 12/1985 | Cooper ................................. 424/128 |

Primary Examiner—Dale R. Ore
Attorney, Agent, or Firm—Steven J. Goldstein; Douglas C. Mohl; Richard C. Witte

[57] ABSTRACT

Topical pharmaceutical compositions containing a specific 6-amino-1,2-dihydro-1-hydroxy-2-iminopyrimidine component and a penetration-enhancing vehicle are disclosed. The vehicle comprises a binary combination of a $C_3$–$C_4$ diol or $C_3$–$C_6$ triol and isocetyl alcohol polar lipid compound. The vehicle provides marked transepidermal and percutaneous delivery of the iminopyrimidine compound. These compositions, when applied topically, act to stimulate the growth of mammalian hair on the body.

10 Claims, No Drawings

PENETRATING TOPICAL PHARMACEUTICAL COMPOSITIONS

This is a continuation of application Ser. No. 874,248 filed June 13, 1986.

TECHNICAL FIELD

The present invention relates to improved topical compositions containing known hydroxy iminopyrimidine pharmaceutical agents, such as Minoxidil. Among other pharmaceutical properties, Minoxidil has been disclosed to be effective for increasing terminal hair growth and for stimulating the conversion of vellus hair to growth as terminal hair.

BACKGROUND OF THE INVENTION

Alopecia (baldness), a deficiency of hair, either normal or abnormal, is primarily a cosmetic problem in humans. It is a deficiency of terminal hair, the broad diameter, colored hair that is readily visible to the eye. However, in the so-called bald person, although there is a noticeable absence of terminal hair, the skin does contain vellus hair (a fine colorless hair) which may require microscopic examination to be seen. This vellus hair may be a precursor to terminal hair.

It is known that the 1,2-dihydro-1-hydroxypyrimidines of formula (I), when used systemically, are useful as antihypertensive agents.

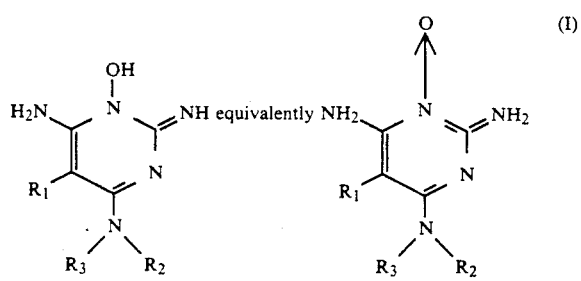

In these compounds, $R_3$ and $R_2$ may be hydrogen, lower alkyl, lower alkenyl, lower aralkyl, or lower cycloalkyl and, taken together, $R_3$ and $R_2$ may be a heterocyclic group, such as aziridinyl, azetidinyl, pyrrolidinyl, piperidino, hexahydroazepinyl, heptamethylenimino, octamethylenimino, morpholino and 4-lower-alkyl-piperazinyl, where each of these heterocyclic groups may have up to three lower alkyl, hydroxy, or alkoxy substituents. $R_1$ may be hydrogen, lower alkyl, lower alkenyl, lower alkoxyalkyl, lower cycloalkyl, lower aryl, lower aralkyl, lower alkaryl, lower alkaralkyl, lower alkoxyaralkyl or lower haloaralkyl. It has also been taught that when these compounds are administered topically they act to stimulate the conversion of vellus hair to terminal hair and prevent the transformation of terminal hair to vellus hair. In short, the topical use of these compounds has been taught to increase the growth of perceivable mammalian hair.

The art is replete with disclosures of topical vehicles which are said to improve the penetration of a variety of pharmaceutical actives through the skin. Indeed, it is well-recognized that the development of such vehicles would provide a very useful method for the delivery of pharmaceuticals. It has been taught that a binary penetration system comprising specific polar lipid cell-envelope disordering compounds, such as oleic acid or methyl laurate, together with specific diol compounds, such as propylene glycol, can be used to topically deliver systemic levels of selected pharmaceutical agents, such as steroids and non-steroidal antiinflammatory agents. However, these vehicles have not been found to be equally effective for enhancing the delivery of all pharmaceutical agents.

In order to be useful as a topical vehicle for a hair-growth stimulating agent, the vehicle must satisfy four stringent requirements:

(1) the vehicle must provide enhanced penetration of the agent through the skin;

(2) the vehicle must have cosmetically-acceptable aesthetics;

(3) the vehicle must not be irritating to the skin; and (4) the vehicle must be preferentially substantive to the scalp or skin rather than to, for example, the comb or clothing. While some vehicles may satisfy several of these criteria, the best vehicles will be optimum for all of them.

It has now been found that hydroxy iminopyrimidine compounds of the formula (I) can be effectively delivered percutaneously by incorporating them into a specific vehicle which provides an exceptional increase in penetration over conventional vehicles. In addition, this vehicle satisfies all four of the requirements set forth above. Thus, the present invention provides an aesthetically acceptable topical vehicle which can enhance the mammalian hair growth effects of the 1,2-dihydro-1-hydroxy-iminopyrimidine compounds, such as Minoxidil. Specifically, it has been discovered that a specific binary surfactant system comprising a polar lipid compound and a diol or triol compound can consistently and dramatically improve the topical delivery of 1,2-dihydro-1-hydroxyiminopyrimidine compounds (formula (I)).

U.S. Pat. No. 3,461,461, Anthony et al, issued Aug. 12, 1969, discloses a class of 6-amino-1,2-dihydro-1-hydroxy-2-iminopyrimidines and describes the use of these compounds as antihypertensive agents. The topical administration of these compounds to stimulate mammalian hair growth is disclosed in U.S. Pat. No. 4,139,619, Chidsey, III, issued Feb. 13, 1979. Standard aqueous solutions, ointments and creams, such as those based on propylene glycol, ethanol, n-methyl-pyrrolidone, or petrolatum are used for the topical formulations. A closely related group of compounds, 6-amino-1,2-dihydro-1-hydroxy-2-imino-4-phenoxypyrimidines, is disclosed in U.S. Pat. No. 3,382,247, Anthony et al, issued May 7, 1968. A process for preparing 6-substituted-4-amino-1,2-dihydro-1-hydroxy-2-iminopyrimidines is taught in U.S. Pat. No. 3,644,364, Anthony, issued Feb. 22, 1972.

U.S. Pat. No. 4,070,462, Ecker, issued Feb. 24, 1978, discloses a topical vehicle which includes (i) 5–15% 1,2-propanediol, 2,3-butanediol or 2-methyl-2,4, propanediol; (ii) 1–3% propylene glycol monostearate; and (iii) petrolatums and waxes to 100%.

European Patent Application 13,459, published July 23, 1980, describes compositions useful in the treatment of acne. These compositions contain benzoyl peroxide, $C_6$–$C_{14}$ primary alcohols, and a diol selected from 1,2-propanediol, 1,2-butanediol, 1,3-butanediol, and 2,3-butanediol.

European Patent Application 43,738, published Jan. 13, 1982, describes compositions for topical application. The compositions described are suitable for effective delivery of lipophilic, pharmacologically-active compounds using primary alcohols or various carboxylate compounds in combination with selected diols.

European Patent Application 95,813, published Dec. 7, 1983, discloses a binary penetration system utilizing a diol and a cell-envelope disordering compound to aid in the penetration of 9-hydroxyethoxymethyl (and related) derivatives of 6- and 2,6-substituted purines. These purine compounds are reported to be effective in the treatment of viral infections, especially herpes, and can be administered parenterally, orally or topically. 9-(2-hydroxyethoxymethyl) guanine is disclosed as being a particularly preferred active.

U.S. Pat. No. 4,552,872, Cooper, et al, issued Nov. 12, 1985, describes topical pharmaceutical compositions containing corticosteroids and a skin penetration enhancing vehicle comprising selected diols and cell-envelope disordering compounds. These compositions are taught to provide systemically active levels of the corticosteroids via topical administration. A similar disclosure is provided in European Patent Application 129,283, published Dec. 27, 1984.

U.S. Pat. No. 4,557,934, Cooper, issued Dec. 10, 1985, describes pharmaceutical compositions for topical application containing any of a wide range of pharmaceutical actives together with a diol compound and 1-dodecyl-azacycloheptan-2-one. See also European Patent 129,284, published Dec. 27, 1984. U.S. Pat. No. 4,537,776, Cooper, issued Aug. 27, 1985, describes pharmaceutical compositions for topical application containing any of a wide range of pharmaceutical actives together with N-(2-hydroxyethyl)pyrrolidone. A similar disclosure is provided in European Patent Application 129,285, published Dec. 27, 1984.

European Patent Application 171,742, published Feb. 18, 1986, discloses topical compositions which provide systemically active doses of opioids to the user. The penetration enhancing topical vehicle comprises at least one of a saturated fatty acid or fatty alcohol of 8-15 carbon atoms or of an unsaturated fatty alcohol or fatty acid of 8-18 carbon atoms, and a pharmaceutical carrier such as propylene glycol.

1,2-propanediol ("propylene glycol") and the $C_{10}$-$C_{14}$ alcohols have been used, separately, in cosmetic and pharmaceutical formulations. In particular, propylene glycol has been described in several articles in the literature as enhancing the penetration of certain pharmacologically active agents, such as the corticosteroids. See Rosuold, J., et al., "Effect of Formulation on In Vitro Release and In Vivo Absorption of Corticosteroids from Ointments", *Medd. Novsk Favm Selsk*, 44, 21-45 (1982); see also, Anjo, D.M., et al., "Methods for Predicting Percutaneous Penetration in Man", *Percutaneous Absorption of Steroids*, pp 31-51, Academic Press, New York, N.Y. (1980).

U.S. Pat. No. 3,535,422, Cox, et al., Oct. 20, 1970, relates to stable benzoyl peroxide compositions containing organic emollients selected from $C_4$-$C_{20}$ aliphatic alcohols, $C_2$-$C_3$ glycols, $C_{12}$-$C_{20}$ fatty acids and their esters, and mixtures thereof.

U.S. Pat. No. 4,070,462, Ecker, issued Jan. 24, 1978, describes topical steroid compositions containing 6% propylene glycol and 1% propylene glycol monostearate.

Canadian Patent 1,072,009, Sipos, issued Feb. 19, 1980, describes topical antimicrobial compositions containing $C_5$-$C_{10}$ straight chain alcohols or $C_{17}$ branched chain alcohols in which the longest chain is $C_5$-$C_{10}$.

CA 92: 153, 181j describes an indomethacin ointment containing 10% propylene glycol and 1.1% disopropanolamine.

B. Idson, *Cosmetics & Toiletries*, 95, 59 (1980), states that the factors affecting drug penetration and, consequently in most cases, effectiveness, are complex. He observes that the vehicle that provides ideal penetration conditions for one drug may prove unsatisfactory for another. The author concludes that prediction is not simple and product suitability must be assessed by human trials.

U.S. Pat. No. 4,299,826, Luedders, issued Nov. 10, 1981, describes a composition for the treatment of acne which includes diisopropyl sebacate in combination with an alcohol as a penetration enhancer for an erythromycin derivative.

SUMMARY OF THE INVENTION

The present invention relates to improved topical compositions and methods for stimulating the growth of hair in humans and animals. The invention is based on the use of specific hydroxy iminopyrimidine compounds together with a well-defined binary mixture of a polar lipid compound and a small polar solvent (diol or triol compound).

The compositions of this invention comprise a safe and effective amount of a specific hydroxy iminopyrimidine compound, as defined below, together with a penetration-enhancing vehicle containing a $C_3$-$C_4$ diol, such as propylene glycol, or a $C_3$-$C_6$ triol, such as 1,2,6-hexanetriol, together with a polar lipid compound selected from $C_{16}$ mono-unsaturated alcohols, $C_{16}$ branched chain saturated alcohols and $C_{18}$ mono-unsaturated and branched chain saturated alcohols, such as oleyl alcohol or isocetyl alcohol. It is preferred that this vehicle be substantially free of saturated, straight chain $C_4$, $C_6$ and $C_{18}$-$C_{20}$ primary alcohols, and $C_4$-$C_{20}$ mono- or dicarboxylic acids. Although topical vehicles containing a wide range of polar lipid compounds are known, it is only by utilizing these specifically-defined $C_{16}$ or $C_{18}$ alcohols that vehicles exhibiting improved skin penetration, no skin irritation, acceptable aesthetics and scalp/skin substantivity can be formulated for the hydroxy iminopyrimidine compounds.

The invention also encompasses regimens for stimulating the growth of hair in humans or animals comprising the topical administration to a human or lower animal of a safe and effective amount of the composition. The composition is applied at the situs where such treatment is required.

DETAILED DESCRIPTION OF THE INVENTION

By "topical administration", as used herein, is meant directly laying on or spreading on outer skin (membrane epidermal tissue) or hair.

By "safe and effective amount", as used herein, is meant a sufficient amount of the composition to provide the desired hair growth stimulation effect at a reasonable benefit/risk ratio attendant with any medical treatment. Within the scope of sound medical judgment, the amount of pharmaceutical active used may vary with the particular condition being treated, the severity of the condition, the cause of the condition, the duration of the treatment, the specific active compound employed, its concentration, the specific vehicle utilized, the general health of the patient, other drugs being administered to the patient, and like factors within the specific knowledge and expertise of the patient or the attending physician.

By "toxicologically-acceptable" or "pharmaceutically-acceptable", as used herein, is meant that drugs, medicaments or inert ingredients which the term describes are suitable for use in contact with the tissues of humans and lower animals without undue toxicity, irritation, allergic response, and the like, commensurate with a reasonable benefit/risk ratio.

By the term "comprising", as used herein, is meant that various other compatible drugs and medicaments, as well as inert ingredients, occlusive agents, and cosmetic vehicles, can be conjointly employed in the compositions and processes of this invention, as long as the critical binary penetration enhancement vehicle and pharmaceutical active are used in the manner disclosed herein. The term "comprising" thus encompasses and includes the more restrictive terms "consisting of" and "consisting essentially of" which characterize the use of the essential ingredients in the manner disclosed herein.

By "application situs", as used herein, is meant a localized area where it is desired that hair growth be stimulated. In humans the application situs can, for example, be on the head, pubic area, upper lip, eyebrows and eyelids. In animals raised for their pelts (for example, mink) the application situs can be over the entire surface of the body to improve the overall pelt for commercial reasons. The present invention can also be used for cosmetic reasons in animals, e.g., application to the skin of dogs or cats having bald patches due to manage or other diseases.

By "penetration-enhancing", as used herein, is meant that the binary penetration enhancing carriers of this invention provide marked transepidermal or percutaneous delivery of the incorporated 6-amino-1,3-dihydro-1-hydroxy-2-iminopyrimidine compound when compared to other compositions at equal chemical potential. This latter aspect is important, since varying solubilities of drugs in different vehicles will necessarily affect their transport across skin. Thus, for example, if a drug is soluble in vehicle A to the extent of 24%, and in vehicle B to the extent of 4%, if the compositions were to be compared at equal percentage concentration, rather than equal chemical potential, the lower solubility carrier will show a misleading six-fold difference in transport over the more soluble vehicle. The simplest way of assuring equal chemical potential for evaluating penetration enhancement is to use saturated solutions or solutions of equal percentage of saturation of pharmacological active in the various vehicles. It should be emphasized that while saturated solutions are useful for comparing the skin penetrating efficacy of vehicles, the compositions of the present invention need not be formulated so as to be saturated with the hydroxy iminopyrimidine component.

By "substantially free", as used herein, is meant that the penetration-enhancing compositions and carriers of the present invention contain less than about 3.5%, preferably less than about 1%, and most preferably less than about 0.5%, of any single or specific compound, or member of the group of compounds, described by this term.

As used herein, all percentages are by weight unless otherwise specified.

The compositions of this invention require, at a minimum, hydroxy iminopyrimidine compound, as defined below, a diol or triol compound (small polar solvent), and a $C_{16}$ or $C_{18}$ alcohol compound (polar lipid). The compositions of this invention may additionally contain optional conventional components which reduce skin irritation or enhance their cosmetic appeal and acceptability, i.e., thickeners, pigments, and the like. Preferably, the compositions are substantially free from penetration-interfering straight chain $C_4$, $C_6$ or $C_{18}$–$C_{20}$ saturated primary alcohols, and $C_4$–$C_{20}$ mono- or dicarboxylic acids.

The hydroxy iminopyrimidine compounds which form the pharmaceutically-active component of the present invention are known in the art to stimulate the growth of mammalian hair when applied topically. These compounds are 6-amino-1,2-dihydro-1-hydroxy-2-iminopyrimidines and have the formula:

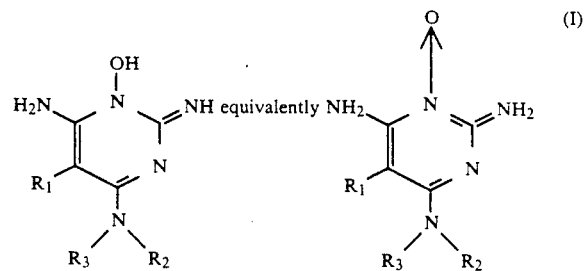

(I)

wherein $R_3$ and $R_2$ are selected from hydrogen, lower alkyl, lower alkenyl, lower aralkyl or lower cycloalkyl. $R_3$ and $R_2$ may also be taken together to form a heterocyclic moiety selected from aziridinyl, azetidinyl, pyrolidinyl, piperidino, hexahydroazepinyl, heptamethylenimino, octamethylenimino, morpholino or 4-lower alkyl-piperazinyl; with each of these heterocyclic moieties having attached as substituents on the carbon atoms 0-3 lower alkyl groups, hydroxy or alkoxy. $R_1$ may be selected from hydrogen, lower alkyl, lower alkenyl, lower alkoxyalkyl, lower cycloalkyl, lower aryl, lower aralkyl, lower alkaryl, lower alkaralkyl, lower alkoxyaralkyl, lower haloaralkyl, and the pharmaceutically acceptable acid addition salts of these compounds.

A particularly preferred compound for use in the present invention is 6-amino-1,2-dihydro-1-hydroxy-2-imino-4-piperidinopyrimidine, in either its free base or hydrochloric acid salt. This compound (II) is identified by the tradename Minoxidil ® and is available commercially as a fully formulated tablet, Loniten ®, from the Upjohn Company, Kalamazoo, Mich. Examples of other suitable acid salts of this compound include the phosphoric acid, acetic acid, citric acid or lactic acid salts.

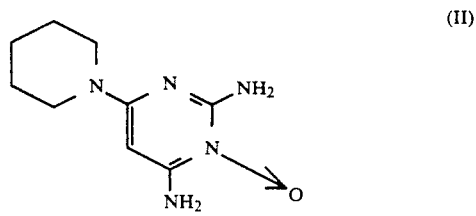

(II)

The hydroxy iminopyrimidine compounds used in the present invention, as well as the methods for synthesizing those compounds, are discussed in detail in the following issued U.S. patents, all of which are incorporated herein by reference: U.S. Pat. No. 3,461,461, Anthony et al., issued Aug. 12, 1969; U.S. Pat. No. 3,382,247, Anthony et al., issued May 7, 1968; U.S. Pat. No. 3,644,364, Anthony, issued Feb. 22, 1972; and U.S. Pat. No. 4,139,619, Chidsey III, issued Feb. 13, 1979.

Compositions of the present invention contain a safe and effective amount of the hydroxy iminopyrimidine active component; preferably the compositions contain from about 0.01% to about 10%, more preferably from about 0.25% to about 5%, most preferably about 1%, of this component. Of course, the level of active component will vary with the nature and cause of the condition being treated, the surface area available for application, the particular vehicle selected, and the precise application regimen.

VEHICLE

The vehicles of the present invention significantly enhance the skin penetration of the hydroxy iminopyrimidine active component. They comprise, at a minimum, a diol or triol (small polar solvent) together with a polar lipid compound.

The $C_3$–$C_4$ diol compounds useful in the compositions and methods of the instant invention include 1,2-propanediol, 1,3-propanediol, 1,2-butanediol, 1,3-butanediol, 1,4-butanediol, or mixtures of these diol compounds. 1,2-propanediol and 1,2-butanediol are preferred diol compounds. 1,2-propanediol is an especially preferred compound, and is preferably used at a level of at least about 7.5% of the total composition. The $C_3$–$C_6$ triol compounds useful herein include, for example, glycerol, 1,2,6-hexanetriol, 1,2,5-pentanetriol, 1,2,4-butanetriol, 1,2,5-hexanetriol, or mixtures of triol compounds. Preferred triols are glycerol and 1,2,6-hexanetriol. Mixtures of diol and triol compounds may also be used.

The polar lipid compounds useful in the compositions and methods of the present invention include $C_{16}$ or $C_{18}$ monounsaturated or branched chain saturated alcohols. Examples of these compounds include $\Delta 9C_{18}:1$ oleyl alcohol, $\Delta 9C_{16}:1$ palmitoleyl alcohol, $\Delta 9C_{14}:1$ myristoleyl alcohol, $C_{14}:0$ myristyl alcohol, $\Delta 9C_{18}:1$ elaidyl alcohol, $\Delta 11C_{18}:1$ vaccenyl alcohol (cis or trans), $\Delta 6C_{18}:1$ petroselinyl alcohol, $\Delta 6C_{18}:1$ petroselaidyl alcohol, and mixtures thereof. Preferred polar lipid compounds include oleyl alcohol, isocetyl alcohol, and mixtures thereof.

Although other polar lipid (cell envelope disordering) compounds, such as oleic acid, methyl laurate, monoolein and myristyl alcohol, have been disclosed for use in certain topical vehicles, it has now been discovered that, in hydroxy iminopyrimidine formulations for use to stimulate hair growth, it is necessary to use the specific above-described alcohols as the polar lipid compound in order to get compositions which enhance skin penetration of the active, do not irritate the skin, are aesthetically acceptable, and are substantive to skin and scalp. This is particularly surprising since oleyl alcohol, a preferred component of the present invention, has been taught in the art to be irritating to the skin when topically applied. Where oleyl alcohol is used in the present invention, it should be used at a level of at least about 0.25% of the total composition.

Binary mixtures of any of the foregoing diol or triol compounds together with polar lipid compounds, in a weight ratio of diol/triol compound: polar lipid compound of from about 1:1 to about 500:1, provide significant enhancement of penetration for the hydroxy iminopyrimidine compound described herein. A ratio of diol/triol compound: polar lipid compound of from about 5:1 to about 100:1 is preferred, and the penetrating components are most preferably present in a ratio of from about 10:1 to about 100:1. In a highly preferred embodiment, the penetrating components are present in a ratio of from about 15:1 to about 50:1.

The compositions of this invention typically contain from about 5% to about 99.9%, and preferably from about 10% to about 99.5%, by weight, of the penetration-enhancing binary mixture of the diol or triol compounds and polar lipid compounds, employing the ratios described above.

The preferences expressed above are predicated solely upon maximizing penetration. In certain topical formulations, however, aesthetic and cosmetic qualities may be of equal or even paramount importance. Accordingly, ranges other than those described above may be preferred. In general, a composition employing a weight:weight ratio of from about 1:1 to about 10:1 will not demonstrate the same degree of penetration enhancement as a system employing the same components at a weight ratio of from about 10:1 to about 50:1. However, such ratios (1:1–10:1) may be preferred for certain vehicles or systems because they frequently produce better aesthetic qualities. It should be noted that while not generally providing maximum penetration, such aesthetically pleasing compositions nonetheless demonstrate a dramatic enhancement of penetration when compared to conventional or art-disclosed vehicles or systems. Compositions comprising a binary mixture at a level of from about 20% to about 45% of the overall composition and employing diol/triol: polar lipid compound weight ratios of from about 4:1 to about 6:1 provide an excellent compromise or balance of cosmetic acceptability and enhanced penetration and are accordingly preferred.

OPTIONAL COMPONENTS

In addition to the components described above, the compositions of this invention may optionally contain a cosmetically acceptable solvent. The solvent, if used, should not significantly interfere with the penetration action of the binary combination, and should preferably evaporate rapidly and completely to leave only the active components of the composition at the site of application. Preferred solvents include ethanol and isopropanol.

Water may be used as a solvent or component in the compositions of the present invention. However, simple addition of water to these compositions may cause some or all of the penetration-enhancing compounds to precipitate out. Such action in the formulation of the compositions of the present invention may significantly reduce the overall effectiveness of the system. In order to prevent this, it is important that the hydroxy iminopyrimidine active be soluble in the compositions of the present invention. One way to accomplish this may be through the formation of an emulsion or gel. Emulsifiers or gelling agents may be used to accomplish this.

Such solvents, i.e., water, ethanol or 2-propanol (isopropanol; isopropyl alcohol), may comprise from 0% to about 90% of the total composition by weight. Ethanol and 2-propanol are preferably present at a level of from 0% to about 85%.

However, certain solvents, cosolvents, excipients, and lipid materials as described below, are preferably avoided in the practice of the present invention. It is thought that such compounds bind or change the solubility of the polar lipids in the binary system such that they can no longer enter the stratum corneum. This inhibition of penetration prevents the disruption or disordering of the lipids of the stratum corneum necessary for altering the barrier properties of skin. Some of these compounds may also act as surface reservoirs and inhibit penetration of the hydroxy iminopyrimidine active across the skin. For example, if dimethylisosorbide, a commonly-used film-forming solvent, is included in the present invention, penetration of the active (e.g., Minoxidil) is inhibited. Thus, such compounds are preferably avoided when formulating the compositions of the present invention. If used, such compounds should generally be used as sparingly as possible, far below art-established levels.

For example, hydrocarbons such as liquid petrolatum (mineral oil, liquid paraffin, paraffin oil), white petrolatum, yellow petrolatum, paraffin, microcrystalline wax, and ceresin are all known generally to be useful as hydrophobic vehicles or structural matrix formers in topical pharmaceutical formulations. However, all of these excipients are capable of significantly interfering with the penetration-enhancing abilities of the present invention. While a certain level of such ingredients can be tolerated in a system which is otherwise particularly effective, in a preferred embodiment of the present invention such ingredients are limited to less than about 10%, and preferably less than about 5%.

Certain straight chain, saturated $C_4$, $C_6$ and $C_{18}$–$C_{20}$ normal fatty alcohols should also be avoided. Stearyl alcohol is an extremely common ingredient in topical formulations. Yet, this alcohol is capable of significant interference with the penetration enhancement of the present vehicle. This alcohol, as well as the $C_{18}$ saturated normal alcohol, is likely to retard the penetration enhancing abilities of the systems of the present invention. Accordingly, in a preferred embodiment, the compositions of the present invention are substantially free of such compounds, i.e., any particular compound should be present at a level of less than about 3.5%, and more preferably at a level less than about 1% by weight of the entire composition. In a highly preferred embodiment the compositions of the present invention contain less than about 0.5% of any specific member of said alcohol group.

Certain fatty acids are also capable of gross interference with penetration by the compositions of the present invention. These acids include the straight chain $C_4$–$C_{20}$ saturated monocarboxylic and dicarboxylic acids. Octanoic and decanoic acid are particularly harmful to the vehicles of the present system. In a preferred embodiment, the compositions of the present invention are substantially free of these acids, i.e., contain less than about 3.5% of any particular member of $C_4$–$C_{20}$ saturated monocarboxylic and dicarboxylic acids, and more preferably less than about 1% of said acids by weight of the entire composition. In a highly preferred embodiment the compositions of the present invention contain less than about 0.5% of any specific member of said acid group.

The compositions of the present invention may additionally contain other compatible adjunct components conventionally found in pharmaceutical compositions, not recited above, at their art-established usage levels. Thus, for example, the compositions may contain additional compatible pharmaceutically-active materials for combination therapy or may contain materials useful in physically formulating various dosage forms of the present invention, such as excipients, dyes, perfumes, fragrances, preservatives, anti-oxidants, opacifiers, thickening agents and stabilizers. Such materials, when added, should be selected so they do not unduly interfere with the penetration enhancement of these compositions. For example, the inclusion of dimethylisosorbide tends to inhibit penetration of the active, while the inclusion of xanthan gum does not. Such formula modifications to improve cosmetic acceptability are well within the skill of workers in the cosmetic and dermatological arts and, by themselves, constitute no part of the present invention.

It can be seen from the foregoing that the compositions of the present invention permit considerable variation, so long as the critical components of hydroxy iminopyrimidine compound, diol or triol compound and polar lipid compound are present within the ranges indicated above and the stated penetration interfering components are minimized. Thus, in addition to conventional topical compositions, such as gels, lotions, salves, ointments and solutions, the compositions of the present invention may be formulated as a shampoo, an aerosol spray, a nonaerosol spray, or a mousse.

METHOD OF USE

It will be appreciated that this invention provides a method for stimulating the growth of hair in humans and lower animals. In addition, the compositions of the present invention may be applied to hairy areas to prevent hair loss. The present invention permits the significantly improved topical application of the hydroxy iminopyrimidine actives defined herein in an aesthetically acceptable, skin substantive composition, without irritating the skin at the site of application.

Topical treatment regimens according to the practice of this invention comprise applying the compositions herein directly to the skin, i.e., at the application situs, usually one to six times daily. The rate of application and duration of treatment will, of course, depend on many factors. A typical safe and effective usage rate for topical treatment is from about 1 mg to about 10 mg of the total topical composition per square centimeter of skin per application. The skilled artisan will appreciate that this application rate will vary with the desired effect, the condition being treated and its cause, its progress and response, the area involved, the severity and nature of the condition being treated, the precise identity of the active and or carriers being used, the presence or absence of penetration-interfering solvents, cosolvents, excipients and lipids, the physical condition of the patient, concurrent therapies being administered, the concentration of the actives or carriers being used, as well as other factors within the particular knowledge of the patent and/or physician within the scope of sound medical judgment. Generally, the compositions of the present invention will be used such that a total of from about 2.5 mg to about 100 mg of the hydroxy iminopyrimidine active will be applied each day.

The compositions can be applied from once every twenty-four hours to once every hour. Application intervals of every 4 hours to every 12 hours are preferred. A treatment regimen of application every 12 hours is particularly preferred because it minimizes the amount of active which is applied at any one time while reducing the inconvenience of frequent applications. However, any treatment regimen which allows a safe and effective amount of hydroxy iminopyrimidine active to reach the afflicted situs can be employed while using the compositions of this invention.

The following nonlimiting examples illustrate the compositions of the present invention. They are conventionally formulated by mixing all components thoroughly.

| Composition I | |
|---|---|
| 6-amino-1,2-dihydro-1-hydroxy-2-iminopyrimidine, free base | 5.0% |
| Propylene Glycol (1,2-propanediol) | 91.0% |
| Oleyl alcohol | 4.0% |
| Composition II | |
| 6-amino-1,2-dihydro-1-hydroxy-2-iminopyrimidine hydrochloride | 1.0% |
| Propylene Glycol (1,2-propanediol) | 94.0% |
| Oleyl alcohol | 5.0% |
| Composition III | |
| 6-amino-1,2-dihydro-1-hydroxy-2-iminopyrimidine, free base | 1.0% |
| Propylene Glycol (1,2-propanediol) | 30.0% |
| Palmitoleyl alcohol | 0.5% |
| Ethanol | 50.0% |
| Water | 18.5% |
| Composition IV | |
| 6-amino-1,2-dihydro-1-hydroxy-2-iminopyrimidine, free base | 5.0% |
| Propylene Glycol (1,2-propanediol) | 30.0% |
| Isocetyl alcohol | 1.0% |
| Ethanol | 50.0% |
| Water | 14.0% |
| Composition V | |
| 6-amino-1,2-dihydro-1-hydroxy-2-iminopyrimidine, free base | 0.5% |
| Propylene Glycol (1,2-propanediol) | 97.5% |
| Oleyl alcohol | 2.0% |
| Composition VI | |
| 6-amino-1,2-dihydro-1-hydroxy-2-iminopyrimidine, free base | 6.0% |
| 1,2-butanediol | 90.0% |
| Isocetyl alcohol | 4.0% |
| Composition VII | |
| 6-amino-1,2-dihydro-1-hydroxy-2-iminopyrimidine, free base | 0.5% |
| 1,3-butanediol | 97.5% |
| Oleyl alcohol | 2.0% |
| Composition VIII | |
| 6-amino-1,2-dihydro-1-hydroxy-2-iminopyrimidine, free base | 0.25% |
| 1,2-butanediol | 97.75% |
| Myristoleyl alcohol | 2.0% |
| Composition IX | |
| 6-amino-1,2-dihydro-1-hydroxy-2-iminopyrimidine, free base | 2.0% |
| 1,3-butanediol | 93.0% |
| Iscocetyl alcohol | 5.0% |
| Composition X | |
| 6-amino-1,2-dihydro-1-hydroxy-2-iminopyrimidine, free base | 2.0% |
| Glycerol | 93.0% |
| Oleyl alcohol | 5.0% |
| Composition XI | |
| 6-amino-1,2-dihydro-1-hydroxy-2-iminopyrimidine, free base | 5.0% |
| 1,2-butanediol | 92.0% |
| Oleyl alcohol | 1.5% |
| Isocetyl alcohol | 1.5% |
| Composition XII | |
| 6-amino-1,2-dihydro-1-hydroxy-2-iminopyrimidine, citrate salt | 1.0% |
| Propylene glycol (1,2-propanediol) | 94.0% |
| Isocetyl alcohol | 5.0% |
| Composition XIII | |
| 6-amino-1,2-dihydro-1-hydroxy-2-iminopyrimidine, lactate salt | 5.0% |
| Propylene Glycol (1,2-propanediol) | 91.0% |
| Vaccenyl alcohol | 4.0% |
| Composition XIV | |
| 6-amino-1,2-dihydro-1-hydroxy-2-iminopyrimidine, free base | 12.0% |
| 1,2,6-hexanetriol | 54.0% |
| Oleyl alcohol | 4.0% |
| Ethanol | 30.0% |
| Composition XVI | |
| 6-amino-1,2-dihydro-1-hydroxy-2-iminopyrimidine, free base | 8.0% |
| 1,3-butanediol | 55.0% |
| Oleyl alcohol | 1.0% |
| Isopropanol | 36.0% |

The following nonlimiting examples illustrate the compositions and the methods of the present invention.

EXAMPLE I—PART B

Composition I is applied to a bald human scalp at a rate of 5 mg of composition per square centimeter of skin three times daily to stimulate the growth of terminal hair. Substantially similar results are obtained when the composition is replaced by compositions II, III, IV or V, above.

PENETRATION STUDIES

The penetration studies demonstrate the penetration-enhancing capabilities of the compositions and methods of the present invention. These studies demonstrate the ability of the compositions of the present invention to enhance penetration of the hydroxy iminopyrimidine compounds described in this application when compared to a propylene glycol or a propylene glycol-containing vehicle formulated without the presence of the critical polar lipid compound, as well as when compared to other topical vehicles known in the art.

The following penetration studies were carried out in the manner described. The procedure is described in Merritt and Cooper, *J. Controlled Release*, 2: 161–162 (1984), incorporated herein by reference. Human skin (heat-separated or dermatomed abdominal epidermis, taken at autopsy, or excised, full thickness hairless mouse skin) is placed in a modified Franz diffusion apparatus in a horizontal position between a lower, capped receptor compartment and an upper, open donor compartment (the experiment may also be run with upper chamber occluded). A normal saline solution is added to the receptor compartment abutting the subcutaneous side of the skin. The test composition (comprising a solution of active or actives added to the carrier at the indicated formulation in a conventional manner by thoroughly mixing) is added to the donor compartment abutting the epidermal side of the skin at the levels indicated.

The receptor solution is kept at a constant temperature of about 37° C. At appropriate or desired intervals (these are the time designations given in the following examples) the diffusate from the receptor compartment is withdrawn through a sidearm. Levels of drug active in the diffusate are measured using standard analytical techniques. Each trial is run on a separate sample of skin.

The following experiments were carried out using human skin. 20 ul doses (7000 ug Minoxidil/cm$^2$) were given at time 0 and 24 hours. The Minoxidil concentration used was 70 g/l and the cell area was 0.2 cm$^2$. Eight replicates were run per formulation tested. The averages are reported in the table below.

| Components | COMPOSITIONS | | | | |
|---|---|---|---|---|---|
| | A | B* | C | D* | E |
| Minoxidil ®[1] | 7 | 7 | 7 | 7 | 7 |
| Propylene Glycol | 93 | 92 | 92 | 88 | 88 |
| Oleyl alcohol | — | 1 | — | 5 | — |
| Azone ®[2] | — | — | 1 | — | 5 |

| Composition | Cumulative amount penetrated (ug/cm$^2$) | | | | Steady State Flux (ug/cm$^2$/hr) |
|---|---|---|---|---|---|
| | 0–4 hrs | 0–7 hrs | 0–24 hrs | 0–48 hrs | 7–48 hrs |
| A | ND[3] | ND | 15 | 29 | 0.7 ± 0.2 |
| B* | 4.3 | 31 | 930 | 3100 | 73 ± 25 |
| C | ND | ND | 15 | 37 | 1.0 ± 0.2 |
| D* | 15 | 81 | 1400 | 3500 | 90 ± 18 |
| E | 6.5 | 47 | 1400 | 3000 | 71 ± 14 |
| variation[4] | +59% −37% | +53% −35% | +25% −20% | +20% −17% | |

*composition of the present invention
[1]6-amino-1,2-dihydro-1-hydroxy-2-iminopyrimidine, free base
[2]1-dodecylazacycloheptan-2-one, a skin penetration enhancing agent available from Nelson Research & Development Corporation, Irvine, California.
[3]Minoxidil not detected in the majority of samples (detection limit = 0.5 ug/cm$^2$)
[4]Pooled standard error of the geometric mean. The unsymmetrical bounds are a consequence of the lognormal distribution.

Using the experimental procedure described above, the ability of several compositions of the present invention to penetrate skin was determined. The control composition contained 1% Minoxidil and a vehicle comprising 15% propylene glycol, 65% ethanol and 20% water. This composition is a topical Minoxidil composition which has been disclosed in the art (eg, U.S. Pat. No. 4,139,619). Compositions of the present invention were then formed by adding oleyl alcohol or isocetyl alcohol such that it comprised 0.5%, 1.0%, 2.5%, 5.0% or 10.0% of the vehicle component. Five replicates were tested per formulation. The cumulative penetration of the active component over a 24 hour period is given in the following table.

These data demonstrate the clear skin penetration benefit provided by the compositions of the present invention when compared with art-disclosed topical formulations of Minoxidil.

| Pentration of Minoxidil (1%) Across Human Skin (15% propylene glycol/65% ethanol/20% water) | | |
|---|---|---|
| | Cumulative Pentration (24 hr.) | |
| | ug/cm$^2$ (x̄ ± SD) | % dose (x̄) |
| Oleyl Alcohol (%) | | |
| 0 | 5.3 ± 4.5 | 0.7 |
| 0.5 | 102.5 ± 40.9 | 14.4 |
| 1.0 | 101.9 ± 12.4 | 14.3 |
| 2.5 | 161.2 ± 101.3 | 22.6 |
| 5.0 | 147.9 ± 37.4 | 20.7 |
| 10.0 | 169.4 ± 35.0 | 23.7 |
| Isocetyl Alcohol (%) | | |
| 0 | 25.2 ± 12.7 | 3.5 |
| 0.5 | 137.8 ± 65.7 | 19.3 |
| 1.0 | 133.8 ± 46.0 | 18.7 |
| 2.5 | 105.7 ± 14.2 | 14.8 |
| 5.0 | 149.5 ± 33.8 | 20.9 |
| 10.0 | 136.0 ± 50.6 | 19.0 |

Using the experimental procedure described above, the ability of several triol-containing compositions of the present invention to penetrate skin was determined. The formulations tested are set forth in the first table, with the penetration results set forth beneath. Five replicates were tested per formulation.

| Penetration of Minoxidil (1%) Across Human Skin Vehicle Composition (% wt/wt) | | | | | | |
|---|---|---|---|---|---|---|
| | 1 | 2 | 3 | 4 | 5 | 6 |
| propylene glycol | 15 | 15 | | | | |
| glycerol | | | 15 | 15 | | |
| 1,2,6-hexanetriol | | | | | 15 | 15 |
| ethanol | 65 | 64 | 65 | 64 | 65 | 64 |
| water | 20 | 20 | 20 | 20 | 20 | 20 |
| oleyl alcohol | | 1 | | 1 | | 1 |
| Cumulative Penetration (24 hr) | | | | | | |
| (x̄ ± SD (ug/cm$^2$) | 31 ± 12 | 194 ± 43 | 54 ± 11 | 80 ± 21 | 70 ± 49 | 102 ± 72 |
| % Dose | 4 | 27 | 6 | 11 | 10 | 14 |

EXAMPLE II

The following compositions were formulated by conventional means. Compositions 1–3 were formulated as lotions and compositions 4–6 were formulated as mousse products. The skin penetration of the Minoxidil active (cumulative over a 24 hour period) was measured using the technique described above. Five replicates ere run per formulation; average values are reported.

| | % Compositions | | | | | |
|---|---|---|---|---|---|---|
| | 1 | 2 | 3 | 4 | 5 | 6 |
| propylene glycol | 15.0 | 10.0 | 10.0 | 10.0 | 12.5 | 15.0 |
| propylene glycol monolactate | | | 5.0 | | | |
| lactamide | | 5.0 | | | | |
| oleyl alcohol | 0.5 | 0.5 | 0.5 | 0.5 | 0.5 | 0.5 |
| ethanol | 64.5 | 64.5 | 64.5 | 20.0 | 20.0 | 20.0 |
| water | 20.0 | 20.0 | 20.0 | 68.1 | 65.6 | 63.1 |
| stearic acid | | | | 1.0 | 1.0 | 1.0 |
| xantahn gum | | | | 0.2 | 0.2 | 0.2 |
| 50% KOH | | | | 0.2 | 0.2 | 0.2 |
| Minoxidil ®[1] | 1.0 | 1.0 | 1.0 | 1.0 | 1.0 | 1.0 |
| Cumulative Penetration (ug/cm$^2$) | 64.8 | 42.0 | 46.7 | 58.1 | 70.6 | 54.5 |

Substantially similar results are obtained when the oleyl alcohol in the above composition is replaced, in whole or in part, by isocetyl alcohol, or when the propylene glycol is replaced in whole or in part, by 1,3-propanediol, 1,2-butanediol, 1,3-butanediol, 1,4-butanediol, glycerol, 1,2,6-hexanetriol, or mixtures thereof.

EXAMPLE III

The following shampoo composition is formulated by conventional means.

| Component | % w/w |
|---|---|
| 6-amino-1,2-dihydroxy-1-hydroxy-2-iminopyrimidine, free base | 1.0 |
| Oleyl alcohol | 0.5 |
| Propylene glycol | 15.0 |
| Zinc Pyrithione | 4.0 |
| Ammonium Lauryl Sulfate | 30.0 |
| Ammonium AE$_3$ Sulfate | 30.0 |
| Ammonium Xylene Sulfonate | 4.5 |
| Coconut Monoethanolamide | 4.0 |
| Ethylene glycol distearate | 3.0 |
| Fragrance, Dye, Preservative & other minors | 1.0 |
| Water | Balance to 100 |

The above composition is used on the scalp once a day (10 grams/usage) as a shampoo to stimulate the growth of terminal hair.

Substantially similar results are obtained when the oleyl alcohol in the above composition is replaced, in whole or in part, by isocetyl alcohol, or when the propylene glycol is replaced, in whole or in part, by 1,3-propanediol, 1,2-butanediol, 1,3-butanediol, 1,4-butanediol glycerol, 1,2,6-hexanetriol, or mixtures thereof.

What is claimed is:

1. A penetration-enhancing pharmaceutical composition for topical application, comprising:

(a) from about 0.01% to about 10% of a hydroxy iminopyrimidine compound having the formula

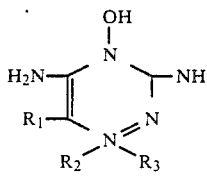

wherein $R_2$ and $R_3$ are selected from the group consisting of hydrogen, lower alkyl, lower alkenyl, lower aralkyl, and lower cycloalkyl, and taken together $R_2$ and $R_3$ may be a heterocyclic moiety selected from the group consisting of aziridinyl, azetidinyl, pyrrolidinyl, piperidine, hexahydroazepinyl, heptamethylenimino, octamethylenimino, morpholino, and 4-lower alkyl piperazinyl, each of said heterocyclic moieties having attached as substituents on the carbon atoms 0-3 lower alkyl groups, hydroxy or alkoxy, and wherein $R_1$ is selected from the group consisting of hydrogen, lower alkyl, lower alkenyl, lower alkoxyalkyl, lower cycloalkyl, lower aryl, lower aralkyl, lower alkaryl, lower alkaralkyl, lower alkoxyaralkyl, and lower haloalkyl, and pharmaceutically acceptable acid addition salts thereof;

(b) 0% to about 90% by weight of a solvent selected from the group consisting of water, ethanol or 2-propanol; and (c) about 5% to about 99.9% by weight of a penetration-enhancing carrier consisting essentially of:

(i) a small polar solvent selected from the group consisting of 1,2-propanediol, 1,2-butanediol, 1,3-butanediol, 2,3-butanediol, $C_3$–$C_6$ triols, or mixtures thereof, and (ii) a polar lipid compound which is isocetyl alcohol; wherein said small polar solvent and said polar lipid compound are present in a ratio of solvent: polar lipid compound of from about 1:1 to about 500:1 by weight.

2. A composition according to claim 1 wherein the hydroxy iminopyrimidine component is selected from 6-amino-1,2-dihydro-1-hydroxy-2-iminopyrimidine and the pharmaceutically acceptable acid addition salts thereof.

3. A composition according to claim 2 wherein the small polar solvent is selected from the group consisting of 1,2-propanediol, 1,2-butanediol, 1,3-butanediol, 2,3-butanediol, or mixtures thereof.

4. A composition according to claim 3 wherein the small polar solvent compound and polar lipid compound are present at a ratio of solvent compound: polar lipid compound of from about 5:1 to about 100:1 by weight.

5. A composition according to claim 4 wherein the small polar solvent compound is selected from the group consisting of 1,2-propanediol, 1,2-butanediol, and mixtures thereof.

6. A composition according to claim 5 wherein the small polar solvent compound is 1,2-propanediol.

7. A method for increasing terminal hair growth in mammalian species comprising the application to mammalian skin at the locale of terminal hair of a safe and effective amount of a composition according to claim 1.

8. A method according to claim 7 wherein the composition is applied in an amount of from about 1 mg/cm$^2$ to about 10 mg/cm$^2$.

9. A method for increasing terminal hair growth in mammalian species comprising the application to mammalian skin at the locale of terminal hair of a safe and effective amount of a composition according to claim 6.

10. A method for increasing the transdermal penetration of pharmaceutically-active hydroxy iminopyrimidine in mammalian species comprising the application to mammalian skin of a safe and effective amount of a composition according to claim 1.

* * * * *